(12) United States Patent
Cates et al.

(10) Patent No.: US 12,239,568 B2
(45) Date of Patent: Mar. 4, 2025

(54) METHODS AND APPARATUS FOR A STOMA COVERING DEVICE

(71) Applicant: MyOstomy, LLC, Chandler, AZ (US)

(72) Inventors: Zachary James Cates, Chandler, AZ (US); Krishna Venkatesh, Chandler, AZ (US)

(73) Assignee: MyOstomy LLC, Chandler, AZ (US)

(*) Notice: Subject to any disclaimer, the term of this patent is extended or adjusted under 35 U.S.C. 154(b) by 0 days.

(21) Appl. No.: 17/739,019

(22) Filed: May 6, 2022

(65) Prior Publication Data
US 2023/0355424 A1    Nov. 9, 2023

(51) Int. Cl.
*A61F 5/445* (2006.01)

(52) U.S. Cl.
CPC ...... *A61F 5/445* (2013.01); *A61F 2005/4455* (2013.01)

(58) Field of Classification Search
CPC ..... A61H 2201/013; A61M 1/08; A61M 1/74; A61M 1/962; A61M 1/64; A61M 2210/1007
See application file for complete search history.

(56) References Cited

U.S. PATENT DOCUMENTS

| | | | | |
|---|---|---|---|---|
| 2,000,710 A | * | 5/1935 | Miller | A61H 9/005 601/6 |
| 2,189,116 A | * | 2/1940 | Niemiec | A61H 9/005 601/6 |
| 3,068,868 A | * | 12/1962 | Skopyk | A61M 1/82 604/314 |
| 3,621,832 A | * | 11/1971 | Fearnside | A61B 5/28 600/387 |
| 5,871,456 A | * | 2/1999 | Armstrong | A61M 1/81 601/14 |
| 5,902,293 A | * | 5/1999 | Liu | A61H 9/005 604/74 |
| 2001/0029956 A1 | * | 10/2001 | Argenta | A61F 13/0226 602/42 |
| 2009/0217931 A1 | * | 9/2009 | Davies | A61B 13/00 128/860 |
| 2010/0145292 A1 | * | 6/2010 | Mayer | A61F 5/445 604/337 |
| 2017/0246025 A1 | * | 8/2017 | Cox | A61F 5/442 |

FOREIGN PATENT DOCUMENTS

CN    214805866    * 12/2020    ............. A61F 5/445

* cited by examiner

*Primary Examiner* — Kai H Weng
*Assistant Examiner* — Alessandro R Del Priore
(74) *Attorney, Agent, or Firm* — Kenneth C. Booth; Booth Udall Fuller, PLC

(57) ABSTRACT

A stoma covering device according to various aspects of the present technology may comprise an open ended body having an internal receiving area configured to receive and be positioned over the stoma to temporarily cover the stoma during the changing process of an ostomy device or wafer. The open ended body may be configured to be held in place in a hands-free manner and without the aid of adhesives, straps, or other mechanical devices. A resilient body may be attached to the open ended body and be used to create a low pressure region within the internal receiving area prior to the stoma covering device being positioned over the stoma.

13 Claims, 3 Drawing Sheets

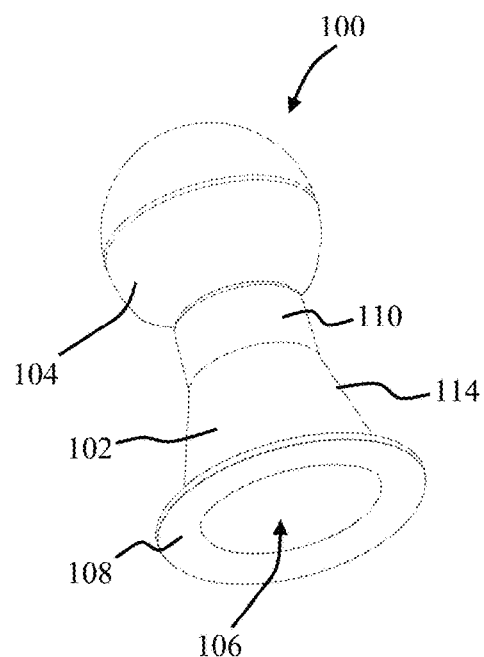 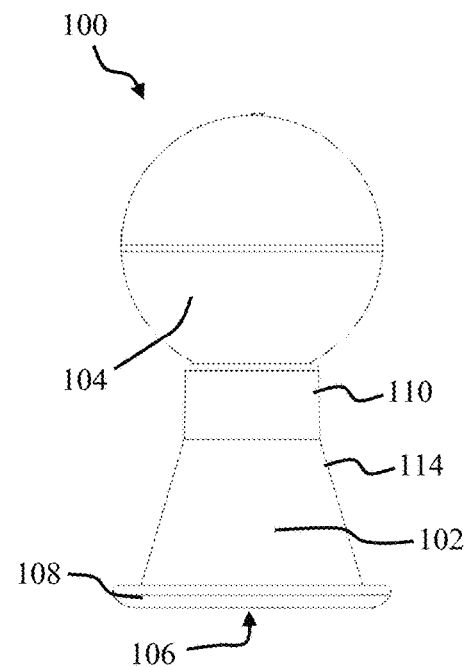
FIG. 1  FIG. 2
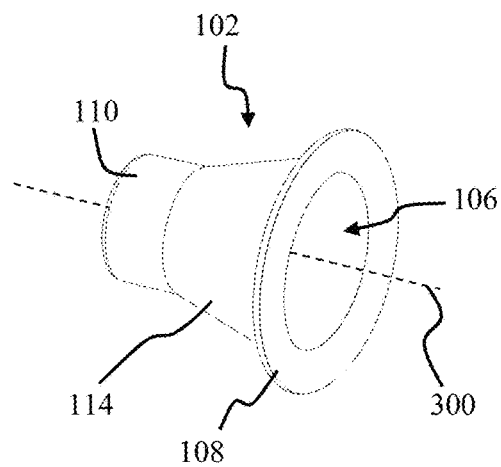 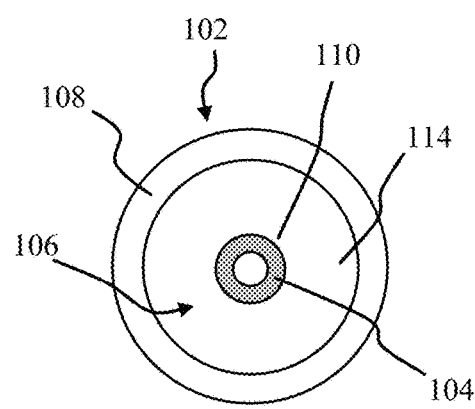
FIG. 3  FIG. 4

METHODS AND APPARATUS FOR A STOMA COVERING DEVICE

BACKGROUND OF THE TECHNOLOGY

When an ostomy appliance or wafer is changed, care must be taken to properly clean and prepare the stoma and surrounding area before a new appliance or wafer can be positioned for use. It may take several minutes for a patient or caregiver to clean and prepare the skin during which time the stoma may be exposed. While the stoma is exposed, leakage from the stoma may occur and can lead to patient discomfort or result in increased efforts to clean and prepare the surrounding area.

SUMMARY OF THE TECHNOLOGY

A stoma covering device according to various aspects of the present technology may comprise an open ended body having an internal receiving area configured to receive and be positioned over the stoma to temporarily cover the stoma during the changing process of an ostomy device or wafer. The open ended body may be configured to be held in place in a hands-free manner and without the aid of adhesives, straps, or other mechanical devices. A resilient body may be attached to the open ended body and be used to create a low pressure region within the internal receiving area prior to the stoma covering device being positioned over the stoma.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

FIG. 1 representatively illustrates a bottom perspective view of a stoma covering device in accordance with an exemplary embodiment of the present technology;

FIG. 2 representatively illustrates a side view of the stoma covering device in accordance with an exemplary embodiment of the present technology;

FIG. 3 representatively illustrates a side perspective view of a cap portion of the stoma covering device in accordance with an exemplary embodiment of the present technology;

FIG. 4 representatively illustrates an end view of the cap portion in accordance with an exemplary embodiment of the present technology;

Figure 5:
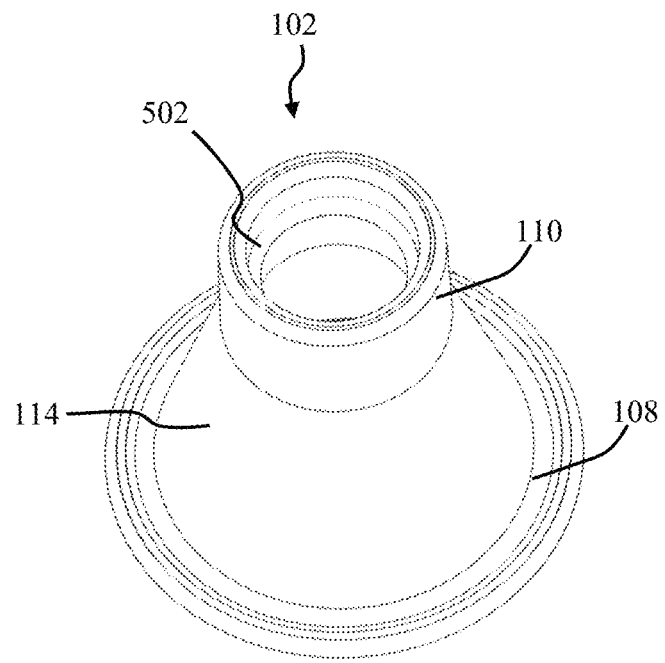
FIG. 5 representatively illustrates a detailed end view of an opposite end of the cap portion shown in FIG. 4 in accordance with an exemplary embodiment of the present technology.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various types of materials and connection devices for coupling components together. In addition, the present technology may be practiced in conjunction with any number of physical activities, and the system described is merely one exemplary application for the technology. Methods and apparatus for a covering device for a stoma according to various aspects of the present technology may operate in conjunction with any suitable materials such as rubber, nylon, plastic, polymers, or other natural or synthetic materials.

Referring to FIGS. 1 and 2, in one embodiment, a stoma covering device 100 may generally comprise a cap portion 102 and a resilient body member 104 connected to the cap portion 102. The cap portion 102 may comprise any suitable device or body for covering the stoma. In one embodiment, the cap portion 102 may comprise a covering body having a first open end 108 of between about 10 mm and about 55 mm in diameter that is configured to be positioned over the stoma such that an outer peripheral edge of the first open end 108 may encircle the stoma and enclose it within an interior receiving portion 106 of the cap portion 102 during use. The outer peripheral edge of the first open end 108 may be configured to create a seal between the cap portion 102 and the user's skin. For example, a reduced pressure volume may be created within the interior receiving portion 106 such that the outer peripheral edge of the first open end 108 may be held against the user's skin as a result of the reduced pressure within the interior receiving portion 106 relative to the ambient pressure acting on the exterior of the cap portion 102 when the stoma covering device 100 is positioned over the stoma. To help form the seal, the outer peripheral edge may be rounded or flared to create a greater surface area for contact between the first open end 108 and the user's skin.

Referring now to FIGS. 3-8, the cap portion 102 may further comprise a second open end 110 located opposite the first open end 108 and a generally conically shaped mid-body section 114 extending between the first and second open ends 108, 110. The second open end 110 may comprise an opening that is smaller than the first open end such that the mid-body section 114 has an increasingly larger cross-sectional area along a longitudinal axis 300 as it progresses from the second open end 110 to the first open end 108. For example, in one embodiment, the second open end 110 may comprise an opening having a diameter of between about 5 mm and about 15 mm. The mid-body section 114 may comprise a sidewall forming a cone shape between the second open end 110 and the first open end 108 such that a cross-sectional area of the interior receiving portion 106 increases along the longitudinal axis 300. The mid-body section 114 may comprise any suitable shape between the first and second ends 108, 110 other than straight and such as: curved; rounded; convex; or concave relative to the longitudinal axis 300.

With particular reference now to FIG. 5, the second open end 110 may comprise a sealing element 502. The sealing element 502 may prevent air leakage out of the second open end 110 when the cap portion 102 and the resilient body member 104 are connected during use. For example, the sealing element 502 may comprise at least one ridge or other surface protruding outward from an interior surface of the second open end 110. The ridge may be configured to press into a surface of the resilient body member 104 to create an airtight seal between the second open end 110 and the resilient body member 104.

The mid-body section 114 may also comprise any suitable length (distance along the longitudinal axis 300) to provide a sufficient interior volume to the interior receiving portion 106 so that the stoma can be enclosed comfortably. For example, the mid-body section 114 may comprise a length of between about 10 mm and about 30 mm.

The cap portion 102 may comprise any suitable material capable of repeated use. For example, the cap portion 102 may be formed of a rigid or semi-rigid plastic or polymer that is capable of being cleaned or sanitized for reuse. Alternatively, the cap portion 102 may comprise a material intended for single use that may be less rigid and less capable of being cleaned such as paper, cardboard, or the like while still being able to withstand a pressure differential between the interior receiving portion 106 and the ambient environment. The material may also be selected based on its density to help reduce the overall weight of the cap portion 102. For example, a lighter weight cap portion 102 may require a lower pressure differential between the interior receiving portion 106 and the ambient environment to hold the stoma covering device 100 in place during use.

Figure 6:
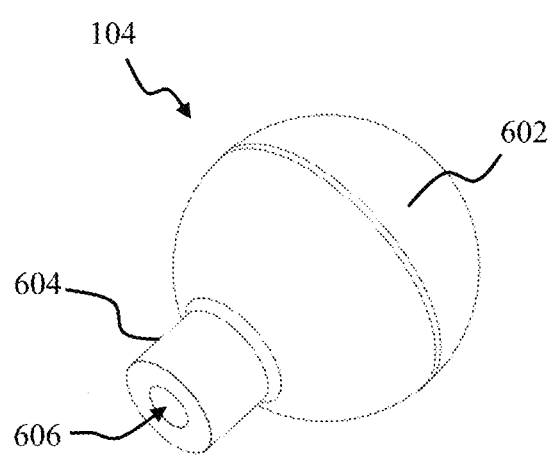
FIG. 6 representatively illustrates a perspective view of a resilient body in accordance with an exemplary embodiment of the present technology.
Figure 7:
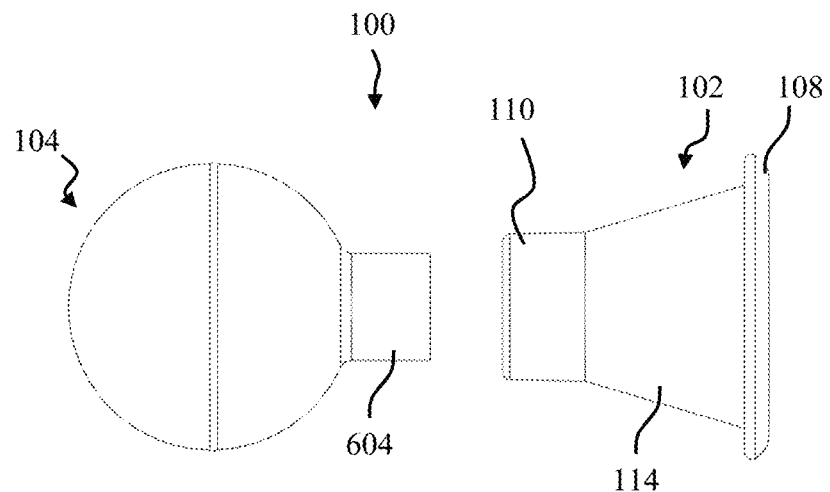
FIG. 7 representatively illustrates an exploded sideview of the cap portion disconnected from the resilient body in accordance with an exemplary embodiment of the present technology.
Figure 8:
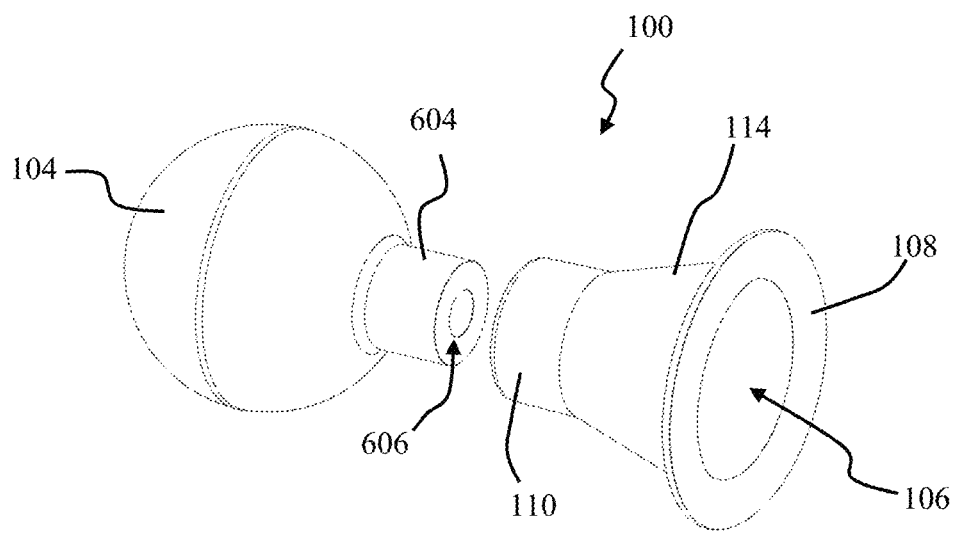
FIG. 8 representatively illustrates an exploded perspective view of the cap portion disconnected from the resilient body in accordance with an exemplary embodiment of the present technology.

Referring now to FIG. 6, the resilient body member 104 is configured to create a low pressure zone within the interior receiving portion 106 of the cap portion 102 to allow the stoma covering device 100 to be held in place over the stoma during use. The resilient body member 104 may comprise any suitable device or system for reducing the pressure within the interior receiving portion 106 when the cap portion 102 is positioned over the stoma and the outer peripheral edge of the first open end 108 is pressed against the user's skin. In one embodiment, the resilient body member 104 may comprise a compressible ball portion 602 and an insertion end 604. In an alternative embodiment, the resilient body member 104 may comprise a pump device configured to pump air out of the interior receiving portion 106 after the stoma covering device 100 is positioned over the stoma.

The compressible ball portion 602 may comprise a round body having an interior volume that is open to the exterior of the compressible ball portion 602 through a passage 606 extending through the insertion end 604. The insertion end 604 may be configured to be inserted into the second open end 110 of the cap portion so that the interior volume of the compressible ball portion 602 is in fluid communication with the interior receiving portion 106 of the cap portion 102.

In operation, during a changing procedure, a user may remove an existing ostomy appliance and replace it with a new ostomy appliance. After the existing ostomy appliance is removed from the stoma, the user may place the first open end 108 of the cap portion 102 over the stoma so that the outer peripheral edge encircles the base of the stoma and the stoma is received into the interior receiving portion 106. Prior to the outer peripheral edge being fully positioned against the user's skin, the user may compress the resilient body member 104 thereby reducing the interior volume inside of the resilient body member 104. Air contained within the interior volume may exit through the first open end 108 of the cap portion 102 via the passage 606 adjacent to the second open end 110.

Then, the outer peripheral edge of the first open end 108 may be seated firmly against the user's skin and the resilient body member 104 is allowed to move from a compressed state to an uncompressed state. As the resilient body member 104 expands to its fully uncompressed state, air is drawn into the interior volume from the interior receiving portion 106 via the passage 606 causing the pressure within the interior volume and the interior receiving portion 106 to decrease below the pressure of the ambient environment surrounding the stoma covering device 100.

The reduction in pressure within the interior receiving portion 106 causes the outer peripheral edge of the first open end 108 to be drawn, or otherwise held, against the user's skin creating a seal so that no air can pass into the interior receiving portion 106. The lower relative pressure inside the interior receiving portion 106 then acts to hold the stoma covering device 100 in place over the stoma allowing the user to have both hands free to clean and prepare the area around the stoma and be able to contain any leakage from the stoma to the interior receiving portion 106. For example, the user may be able to remove an existing ostomy wafer, clean and condition the skin around the stoma, place a new ostomy wafer, without having to hold the stoma covering device 100 in place. When the user is ready to place a new ostomy device over the stoma, the user may remove the stoma covering device 100 by separating the outer peripheral edge of the first open end 108 from the user's skin and thereby allowing the pressure within the interior receiving portion 106 and interior volume of the resilient body 104 to equalize with the ambient conditions. A further benefit is that any leaked material from the stoma may be collected into the interior receiving portion 106 so it may be discarded. The stoma covering device 100 may then be cleaned and reused.

The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Although embodiments of the present technology have been described with reference to use with a stoma, the technology should not be viewed as being limited in that respect.

The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the components and/or elements recited in any apparatus embodiment may be assembled or otherwise operationally configured in a variety of permutations to produce substantially the same result as the present technology and are accordingly not limited to the specific configuration recited in the specific examples.

As used herein, the terms "comprises," "comprising," or any variation thereof, are intended to reference a non-exclusive inclusion, such that a process, method, article, composition or apparatus that comprises a list of elements does not include only those elements recited but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same. Any terms of degree such as "substantially," "about," and "approximate" as used herein mean a reasonable amount of deviation of the modified term such that the end result is not significantly changed. For example, these terms can be construed as including a deviation of at least ±5% of the modified term if this deviation would not negate the meaning of the word it modifies.

The present technology has been described above with reference to exemplary embodiments. However, changes and modifications may be made to the exemplary embodiments without departing from the scope of the present technology. These and other changes or modifications are intended to be included within the scope of the present technology, as expressed in the following claims.

The invention claimed is:

1. A two-piece stoma covering device consisting of:
   a stoma cap portion for use in cleaning and preparing a stoma protruding from a user and a compressible ball portion removably connected to the stoma cap portion for use in creating negative pressure within the mid-body section, the stoma cap comprising:
      a first open end with a first diameter of between 10 mm and 55 mm, the first open end having an outer peripheral edge forming a surface curving outwardly and back towards the first open end, the first open end configured to receive at least a portion of a stoma therein when the radiused lip is positioned around the portion of the stoma;
      a second open end having a single peripheral outer edge having a second diameter of between 5 mm and 15 mm, the second open end having a cylindrical outer shape and at least one surface protruding inward from an interior surface of the second open end;
      a generally conically shaped mid-body section having a continuous inner wall extending between the first open end and the second open end, the continuous inner wall being continuous in that it has no other openings between the first open end and the second open end, the mid-body section having a length of between 10 mm and 30 mm;
   the compressible ball portion comprising:
      a compressible ball having an air chamber, a single passage extending from the air chamber having a diameter smaller than a widest diameter of the air chamber and a length longer than the single passage's diameter, and a continuous inner wall surrounding the air chamber, the continuous inner wall being continuous in that it has no other openings other than the single passage, the compressible ball formed of a resilient material configured to compress and uncompressed the air chamber through manual manipulation by the user;
      an insertion end extending from the compressible ball, the single passage extending through the insertion end, the insertion end having a cylindrical outer shape sized to mate with the second open end and seat against the at least one surface protruding inward from the interior surface of the second end to create a seal between the compressible ball portion and the stoma cap portion;
   wherein when the seal is created between the compressible ball portion and the stoma cap portion and the stoma cap portion is placed over the stoma so that at least a portion of the stoma is received into the stoma cap, manual manipulation of the compressible ball portion by the user creates negative pressure within the mid-body section through the single passage such that the two-piece stoma covering device is maintained in its location to the stoma in a hands-free manner without any manual support by the user or any other support except by the negative pressure throughout the user cleaning and conditioning the skin around the stoma and placing an ostomy wafer around the two-piece stoma covering device and stoma and against the user's skin surrounding the stoma.

2. A two-piece stoma covering device consisting of:
   a stoma cap portion for use in cleaning and preparing a stoma protruding from a user and a compressible ball portion connected to the stoma cap portion for use in creating negative pressure within the mid-body section, the stoma cap comprising:
      a first open end with a first diameter, the first open end having an outer peripheral edge configured to receive at least a portion of a stoma therein;
      a second open end having a peripheral outer edge having a second diameter, the second open end having a cylindrical outer shape;
      a mid-body section having a continuous inner wall extending between the first open end and the second open end, the continuous inner wall being continuous in that it has no otheropenings between the first open end and the second open end;
   the compressible ball portion comprising:
      a compressible ball having an air chamber, a passage extending from the air chamber and a continuous inner wall surrounding the air chamber, the continuous inner wall being continuous in that it has no other openings other than the passage, the compressible ball formed of a resilient material configured to compress and uncompress the air chamber through manual manipulation by the user;
      an insertion end extending from the compressible ball, the passage extending through the insertion end, the insertion end having a cylindrical outer shape sized to engage with the second open end to create a seal between the compressible ball portion and the stoma cap portion;
   wherein when the stoma cap portion is placed over the stoma so that at least a portion of the stoma is received into the stoma cap, manual manipulation of the compressible ball portion by the user creates negative pressure within the mid-body section through the single passage such that the two-piece stoma covering device is maintained in its location to the stoma in a hands-free manner without any manual support by the user or any other support except by the negative pressure throughout the user cleaning and conditioning the skin around the stoma and placing an ostomy wafer around the two-piece stoma covering device and stoma and against the user's skin surrounding the stoma.

3. The two-piece stoma covering device of claim 2, wherein the first diameter is between 10 mm and 55 mm, and the second diameter is between 5 mm and 15 mm, and the mid-body section has a length of between 10 mm and 30 mm.

4. The two-piece stoma covering device of claim 2, wherein the passage has a diameter smaller than a widest diameter of the air chamber.

5. The two-piece stoma covering device of claim 2, wherein the outer peripheral edge forms a surface curving outwardly and back towards the first open end.

6. The two-piece stoma covering device of claim 2, wherein the second open end comprising at least one surface protruding inward from the interior surface of the second end.

7. The two-piece stoma covering device of claim 6, wherein the seal is created between the at least one surface and the insertion end of the compressible ball.

8. A two-piece stoma covering device consisting of:
a stoma cap portion for use in cleaning and preparing a stoma protruding from a user and a compressible ball portion connected to the stoma cap portion for use in creating negative pressure within the mid-body section, the stoma cap comprising:
  a first open end with a first diameter between 10 mm and 55 mm, the first open end having an outer peripheral edge configured to receive at least a portion of a stoma therein;
  a second open end having a peripheral outer edge having a diameter between 5 mm and 15 mm, the second open end having a cylindrical outer shape;
  a mid-body section having a continuous inner wall extending between the first open end and the second open end, the continuous inner wall being continuous in that it has no otheropenings between the first open end and the second open end, the mid-body section having a length of between 10 mm and 30 mm;
the compressible ball portion comprising:
  a compressible ball having an air chamber, a single passage extending from the air chamber, and a continuous inner wall surrounding the air chamber, the continuous inner wall being continuous in that it has no other openings other than the single passage, the compressible ball formed of a resilient material configured to compress and uncompress the air chamber;
  an insertion end extending from the compressible ball and having a cylindrical outer shape sized to mate with the second open end to create a seal between the compressible ball portion and the stoma cap portion;
wherein when the stoma cap portion is placed overthe stoma so that at least a portion of the stoma is received into the stoma cap, manual manipulation of the compressible ball portion by the user creates negative pressure within the mid-body section through the single passage such that the two-piece stoma covering device is maintained in its location to the stoma in a hands-free manner without any manual support by the user or any other support except by the negative pressure throughout the user cleaning and conditioning the skin around the stoma and placing an ostomy wafer around the two-piece stoma covering device and stoma and against the user's skin surrounding the stoma.

9. The two-piece stoma covering device of claim 8, wherein the passage has a diameter smaller than a widest diameter of the air chamber.

10. The two-piece stoma covering device of claim 8, wherein the outer peripheral edge forms a surface curving outwardly and back towards the first open end.

11. The two-piece stoma covering device of claim 8, wherein the second open end comprising at least one surface protruding inward from the interior surface of the second end.

12. The two-piece stoma covering device of claim 11, wherein the seal is created between the at least one surface and the insertion end of the compressible ball.

13. The two-piece stoma covering device of claim 8, wherein the compressible ball portion is removable connected to the stoma cap portion.

* * * * *